(12) United States Patent
Olson (10) Patent No.: US 9,283,294 B2
(45) Date of Patent: Mar. 15, 2016

(54) DEVICE AND METHOD FOR REDUCING A TRANSFER OF MICROORGANISMS BY MANUAL CONTACT

(75) Inventor: Douglas Glenn Olson, Edmonton, CA (US)

(73) Assignee: OUTBREAKER SOLUTIONS INC., Edmonton (CA)

( * ) Notice: Subject to any disclaimer, the term of this patent is extended or adjusted under 35 U.S.C. 154(b) by 0 days.

(21) Appl. No.: 14/123,627

(22) PCT Filed: Jun. 16, 2011

(86) PCT No.: PCT/CA2011/000710
§ 371 (c)(1),
(2), (4) Date: Jan. 29, 2014

(87) PCT Pub. No.: WO2012/171092
PCT Pub. Date: Dec. 20, 2012

(65) Prior Publication Data
US 2014/0134095 A1 May 15, 2014

(51) Int. Cl.
*A61L 2/00* (2006.01)
*A61L 2/23* (2006.01)
*A01N 59/08* (2006.01)
*E05B 1/00* (2006.01)

(52) U.S. Cl.
CPC . *A61L 2/23* (2013.01); *A01N 59/08* (2013.01); *E05B 1/0069* (2013.01)

(58) Field of Classification Search
CPC .................................. A61L 2/23; A01N 25/34
USPC .......................................................... 422/28
See application file for complete search history.

(56) References Cited

U.S. PATENT DOCUMENTS

| | | | |
|---|---|---|---|
| 2,142,825 A | 1/1939 | Patten | |
| 2,527,955 A | 10/1950 | Pagel | |
| 2,599,436 A | 6/1952 | Dancy | |
| 3,314,748 A | 4/1967 | Miller | |
| D211,398 S | 6/1968 | Hall | |
| 3,618,759 A | 11/1971 | Kolasinski et al. | |
| 4,008,351 A | 2/1977 | Inoue et al. | |
| 4,171,776 A | 10/1979 | Pagliaro | |
| 4,658,469 A | 4/1987 | Hawkins | |

(Continued)

FOREIGN PATENT DOCUMENTS

CN 201395914 2/2010
CN 102010795 A * 4/2011

(Continued)

OTHER PUBLICATIONS

English Translation of CN 102010795 A provided by espace.net: Yahui Xing; Bactercidal Environmental-Friendly Bleaching Salt; Apr. 13, 2014.*
"Door Handle Disinfector" by Hygiene-shop.eu http://www.hygiene-shop.eu/index.php/en/Door-handle-Disinfector/c-KAT206/a-HS0000107?sid6125093BC90E4FCA9249E9DD7BAC9D71=d46a2f6a469aBe9669194ad3ea7ba9d2 Available on the Internet at least as early as Dec. 2009 (2 pages).

(Continued)

*Primary Examiner* — Kevin Joyner
(74) *Attorney, Agent, or Firm* — Terrence N. Kuharchuk; Rodman & Rodman LLP (57) ABSTRACT

A manual contact device including an antimicrobial contact surface, wherein the antimicrobial contact surface includes sodium chloride. A method for reducing a transfer of microorganisms by manual contact with a manual contact device, including providing the manual contact device with an antimicrobial contact surface, wherein the antimicrobial contact surface includes sodium chloride.

18 Claims, 8 Drawing Sheets

(56) References Cited

U.S. PATENT DOCUMENTS

| | | | |
|---|---|---|---|
| 4,832,942 A | | 5/1989 | Crace |
| 4,856,140 A | * | 8/1989 | Visco et al. ............. 16/412 |
| 4,953,703 A | | 9/1990 | Virginio |
| 5,654,013 A | | 8/1997 | Taylor et al. |
| 5,824,407 A | | 10/1998 | Hayashi et al. |
| 5,869,104 A | | 2/1999 | Taylor et al. |
| 5,882,667 A | | 3/1999 | Jones |
| 5,987,645 A | | 11/1999 | Teaster |
| 6,073,274 A | | 6/2000 | McQueen |
| 6,298,521 B1 | | 10/2001 | Butterfield |
| 6,350,475 B1 | | 2/2002 | Taylor et al. |
| 6,352,724 B1 | | 3/2002 | Taylor et al. |
| 6,353,971 B1 | | 3/2002 | Krawezyk |
| 6,508,383 B2 | | 1/2003 | Lidahl et al. |
| 6,546,594 B1 | | 4/2003 | Wills |
| 6,638,364 B2 | | 10/2003 | Harkins et al. |
| 6,645,435 B2 | | 11/2003 | Dawson et al. |
| 6,789,695 B1 | | 9/2004 | Gaudreau |
| 6,821,325 B1 | | 11/2004 | Williams et al. |
| 6,874,697 B2 | | 4/2005 | Callueng |
| 2006/0006678 A1 | | 1/2006 | Herron, Jr. |
| 2006/0010652 A1 | | 1/2006 | Kellaher et al. |
| 2006/0153733 A1 | | 7/2006 | Sassoon |
| 2007/0254015 A1 | | 11/2007 | Ishikawa et al. |
| 2007/0294819 A1 | * | 12/2007 | Levesque ............. 4/524 |
| 2010/0209573 A1 | | 8/2010 | Jo et al. |

FOREIGN PATENT DOCUMENTS

| | | |
|---|---|---|
| EP | 0814817 | 5/2003 |
| EP | 2098664 | 9/2009 |
| GB | 8903 | 0/1913 |
| GB | 2353283 | 2/2001 |
| GB | 2442440 | 4/2008 |
| JP | 2212313 | 8/1990 |
| JP | 6321531 | 11/1994 |
| JP | 6321532 | 11/1994 |
| JP | H07-241756 | 9/1995 |
| JP | 11-166332 | 6/1999 |
| JP | 2001-149797 | 6/2001 |
| JP | 2010-106521 | 5/2010 |
| KR | WO2006025642 | 3/2006 |
| SK | WO2009105046 | 8/2009 |

OTHER PUBLICATIONS

"Purleve Hygienic Door Handle Solution" http://www.purleve.com/features.asp Available on the Internet at least as early as Jun. 2009 (10 pages).

"Door Knob Gripper" by Easy Comforts http://www.easycomforts.com/EasyComforts/Shopping/ProductDetail.aspx?CID=Aids+for+Daily+Living&SCID=Aids+for+Daily+Living&ProductID=BC00337816&Sourcecode=30509000001&mr:trackingCode=3BEB371F-6EA8-DE11-93DB-0019B9C043EB&mr:referralID=NA Available on the Internet at least as early as Apr. 20, 2010 (3 pages).

"A Clean Exit" http://www.cleanlink.com/sm/article/A-Clean-Exit-10465 Available on the Internet at least as early as Apr. 20, 2010 (3 pages).

"Gamma Genuine Himalayan Crystal Salt" http://www.himalayansalt.com/saltware-tm.php Downloaded Dec. 13, 2010; Copyright 2001-2010 by Gamma Salt Cristal Ltd. (5 pages).

"100% Natural Antibacterial Himalayan Salt Egg Deodorant" http://www.weirdstuff.ca/products/100-natural-antibacterial-hi . . . Downloaded Dec. 13, 2010; Copyright 2008 Weird Stuff (1 page).

"Natural Salt Bath Soap" http://www.chinaqualitycrafts.com/view/33364292/natural_salt . . . Downloaded Dec. 13, 2010 (3 pages).

"Himalayan Salt-Bricks, Plates and Salt Blocks" http://www.saltworks.us/himalayan-plates-bricks-blocks.html Downloaded Dec. 13, 2010; Copyright 2001-2010 SaltWorks™ (5 pages).

"Ask a Scientist—Sodium Chloride (NaCl) and Bacteria" http://www.newton.dep.anl.gov/askasci/mole00/mole00093.htm Downloaded Dec. 9, 2010 (2 pages).

"Warwick Salt" http://www.selwarwick.com/en/products/AdoucicisseursEau-Sel . . . Downloaded Dec. 8, 2010; Copyright 2008 Sel Warwick (1 page).

"Windsor Salt"—The Canadian Salt Company Limited http://windsorsalt.com/household/household1.html.htm Downloaded Dec. 8, 2010 (3 pages).

"Letters: Hot Salt Water Mouth Baths", British Dental Journal, vol. 195, No. 1, Jul. 12, 2003 (2 pages).

English translation of the Japanese Official Action dated May 19, 2014 listing two prior art references, entitled: "Notification of Reasons for Rejection".

* cited by examiner

DEVICE AND METHOD FOR REDUCING A TRANSFER OF MICROORGANISMS BY MANUAL CONTACT

TECHNICAL FIELD

A device and a method for reducing a transfer of microorganisms by manual contact.

BACKGROUND OF THE INVENTION

The term "microorganisms" may apply generally to microscopic life forms such as single cell organisms, certain multi-cell organisms, and viruses. Examples of organisms which may be considered to be microorganisms include bacteria, fungi, and viruses.

The term "antimicrobial" describes agents and/or substances which may kill or inhibit the growth and/or reproduction of microorganisms.

Harmful microorganisms may cause infections and disease in humans and/or animals. Such harmful microorganisms may be transferred between humans and animals in many ways, including by direct contact or through various forms of indirect transfer mechanism.

One common form of indirect transfer mechanism for harmful microorganisms is through manual contact with inanimate objects. For example, a first person may touch an object such as a railing or a door handle with his or her hand in order to cause microorganisms to be transferred from the hand of the first person to the object, while a second person may touch the object with his or her hand in order to cause microorganisms to be transferred from the object to the hand of the second person.

Depending upon the microorganism and the environment, a microorganism may remain alive on an object for minutes, hours, days, or even longer. As a result, microorganisms transferred by a first person to an object may be capable of being transferred to many persons, particularly in high traffic areas where manual contact with the object is frequent.

In many circumstances, the likelihood of transfer of microorganisms through manual contact with an object may be increased because the object may be comprised of, may consist of, or may consist essentially of a manual contact device for facilitating manual contact with the object. Non limiting examples of manual contact devices include a door knob, a door handle, a door push plate, a door push bar, a light switch, a railing, a tap handle, a toilet flush actuator, and a dispenser actuator.

A manual contact device typically includes a contact surface, which is the location on the manual contact device where manual contact is intended or likely to occur. The contact surface may therefore be exposed to large numbers of microorganisms, and large numbers of microorganisms may reside on the contact surface.

Various attempts have been made in the prior art to provide manual contact devices and/or contact surfaces which have antimicrobial properties. Examples of such attempts are described in U.S. Pat. No. 2,527,955 (Pagel), U.S. Pat. No. 4,832,942 (Crace), U.S. Pat. No. 5,882,667 (Jones), U.S. Pat. No. 6,298,521 (Butterfield), U.S. Pat. No. 6,546,594 (Wills), U.S. Pat. No. 6,821,325 (Williams et al), U.S. Patent Application Publication No. US 2006/0006678 A1 (Herron, Jr.), and U.S. Patent Application Publication No. US 2006/0010652 A1 (Kellaher et al).

Sodium chloride (i.e., salt) has historically been used as a food preservative, because many microorganisms have difficulty living, growing and/or reproducing in a saline environment. An explanation of this phenomenon is that subjecting microorganisms such as bacteria to a saline environment causes dehydration of the microorganism, which inhibits the microorganism from growing and which may eventually result in death of the microorganism.

None of the above referenced attempts in the prior art to provide manual contact devices and/or contact surfaces which have antimicrobial properties have used sodium chloride (i.e., salt) to provide the antimicrobial properties.

SUMMARY OF THE INVENTION

References in this document to orientations, to operating parameters, to ranges, to lower limits of ranges, and to upper limits of ranges are not intended to provide strict boundaries for the scope of the invention, but should be construed to mean "approximately" or "about" or "substantially", within the scope of the teachings of this document, unless expressly stated otherwise.

The present invention is directed at a manual contact device having antimicrobial properties. The present invention is also directed at a method for reducing a transfer of microorganisms by manual contact with a manual contact device, which includes providing the manual contact device with antimicrobial properties. The present invention is particularly directed at the use of sodium chloride (i.e., salt) to provide the antimicrobial properties to the manual contact device.

As used herein, the term "microorganisms" includes microscopic life forms such as single cell organisms, microscopic multi-cell organisms, and viruses. Non limiting examples of microorganisms include bacteria, fungi, and viruses.

As used herein, the term "antimicrobial" or "antimicrobial properties" means having the effect of killing or inhibiting the growth and/or reproduction of one or more types or forms of microorganism.

As used herein, "manual contact" means any contact by a human or animal with an object, including direct contact with hands, feet and/or other body parts and/or indirect contact with hands, feet and/or other body parts through clothing, protective apparel and/or protective gear.

As used herein, a "manual contact device" means any structure, device or apparatus which may be provided to facilitate manual contact with an object. An object may be any structure, device or apparatus. A manual contact device may be attached to or connected with an object, may be integrally formed with an object, or an object may be formed from a manual contact device. As a result, an object may be comprised of a manual contact device, an object may consist of a manual contact device, or an object may consist essentially of a manual contact device. Non limiting examples of manual contact devices include a door knob, a door handle, a door push plate, a door push bar, a light switch, a railing, a tap handle, a toilet flush actuator, and a dispenser actuator.

As used herein, a "contact surface" means a location or an area on a manual contact device where manual contact is intended or likely to occur. A contact surface may be attached to or connected with a manual contact device, may be integrally formed with a manual contact device, or a manual contact device may be formed from a contact surface. As a result, a manual contact device may be comprised of a contact surface, a manual contact device may consist of a contact surface, or a manual contact device may consist essentially of a contact surface.

As used herein, an "antimicrobial contact surface" means a contact surface which has antimicrobial properties.

Within the scope of the invention, the sodium chloride may be provided in any amount, concentration and/or form in order to provide the antimicrobial properties to the manual contact device. In some embodiments, the sodium chloride may be provided in a solid form as a salt block. In some embodiments, the sodium chloride may be provided in a liquid form as a solution or dispersion containing sodium chloride. In some embodiments, the sodium chloride may be provided in a substantially pure form in which additives and/or impurities are minimized.

In some embodiments, the manual contact device may be comprised of an antimicrobial contact surface and the antimicrobial contact surface may be comprised of, may consist of, or may consist essentially of the sodium chloride. In some embodiments, the antimicrobial contact surface may be a salt block, and the salt block may be comprised of, may consist of, or may consist essentially of the sodium chloride.

In some embodiments, the sodium chloride may be deposited as a deposit on the manual contact device in order to provide the antimicrobial contact surface. The sodium chloride may be deposited on the manual contact device in any suitable manner. In some embodiments, the manual contact device may be contacted with a solution and/or dispersion containing sodium chloride in order to cause deposition of the sodium chloride on the manual contact device. In some embodiments, the manual contact device may be contacted with a solution and/or dispersion containing sodium chloride by spraying the manual contact device with the solution and/or dispersion. In some embodiments, the manual contact device may be contacted with a solution and/or dispersion containing sodium chloride by immersing the manual contact device in the solution and/or dispersion.

In an exemplary apparatus aspect, the invention is a manual contact device comprising an antimicrobial contact surface, wherein the antimicrobial contact surface is comprised of sodium chloride.

In an exemplary method aspect, the invention is a method for reducing a transfer of microorganisms by manual contact with a manual contact device, the method comprising providing the manual contact device with an antimicrobial contact surface, wherein the antimicrobial contact surface is comprised of sodium chloride.

In some embodiments, the antimicrobial contact surface may consist essentially of sodium chloride, wherein an antimicrobial contact surface may be considered to consist essentially of sodium chloride if it contains only trace amounts or only insignificant amounts of substances in addition to sodium chloride. As non-limiting examples, table salt, naturally occurring salt blocks and manufactured salt blocks may all typically be considered to consist essentially of sodium chloride, despite the presence of minor amounts of other substances. In some embodiments, the antimicrobial contact surface may be considered to consist essentially of sodium chloride if it contains at least about ninety five (95) percent sodium chloride by weight.

In some embodiments, the method may be further comprised of manually contacting the antimicrobial contact surface. The antimicrobial contact surface may be manually contacted in any manner. The antimicrobial contact surface may be manually contacted one or more times by one or more persons. In some embodiments, manually contacting the antimicrobial contact surface may be comprised of touching and/or grasping the antimicrobial contact surface with a hand.

In some embodiments in which the antimicrobial contact surface includes a salt block, the salt block may be attached to the manual contact device. In some embodiments in which the antimicrobial contact surface includes a salt block, the manual contact device may be formed from the salt block. In some embodiments in which the antimicrobial contact surface includes a salt block, the manual contact device may consist essentially of the salt block.

In some embodiments, the salt block may be a naturally occurring salt block. In some embodiments, the salt block may be a manufactured salt block. The manufactured salt block may be manufactured in any manner. In some embodiments, the salt block may be manufactured by compressing particles of sodium chloride so that the salt block is comprised of compressed particles of sodium chloride.

In some embodiments in which the antimicrobial contact surface includes a deposit of deposited sodium chloride, the deposit may cover all or a portion of the manual contact device, and the deposit may have any thickness.

BRIEF DESCRIPTION OF DRAWINGS

Embodiments of the invention will now be described with reference to the accompanying drawings, in which.

DETAILED DESCRIPTION

Exemplary embodiments of the apparatus of the invention are depicted in FIGS. 1-12. The invention is a manual contact device (20) comprising an antimicrobial contact surface (22). In some exemplary embodiments, the antimicrobial contact surface (22) is a salt block (24) comprising sodium chloride. In some exemplary embodiments, the antimicrobial contact surface (22) is a deposit (26) of sodium chloride which is deposited on the manual contact device (20).

In some exemplary embodiments, the manual contact device (20) may be associated with an object (28). The manual contact device (20) may be associated with the object (28) by being attached to or connected with the object (28), by being integrally formed with the object (28), or the object (28) may be formed from the manual contact device (20). For example, in some embodiments, the object (28) may be a plumbing tap, a door, an electrical switch plate, a toilet, a dispenser such as a paper towel dispenser or a soap dispenser, or the object (28) may be any other suitable structure, device or apparatus. In some exemplary embodiments, the object (28) may be comprised of, may consist of, or may consist essentially of the manual contact device (20).

In some exemplary embodiments which comprise a salt block (24), the salt block (24) may be a naturally occurring salt block comprised of halite. Any type of halite and halite from any source may be suitable for use in the invention as long as the salt block (24) does not exhibit properties which significantly render the salt block (24) unsuitable or unsafe for manual contact. In some particular embodiments, the naturally occurring salt block may be a Himalayan salt block.

Alternatively, in some exemplary embodiments which comprise a salt block (24), the salt block (24) may be a manufactured salt block comprised of particles of sodium chloride which are physically and/or chemically united together in order to provide the salt block (24). Any type of manufactured salt block may be suitable for use in the invention as long as the salt block (24) does not exhibit properties which significantly render the salt block (24) unsuitable or unsafe for manual contact.

The particles of sodium chloride in a manufactured salt block may be united together in any manner. As a first non-limiting example, the particles of sodium chloride in a manufactured salt block may be united together with a binding agent. As a second non-limiting example, the particles of sodium chloride in a manufactured salt block may be united together by compressing the particles so that the manufactured salt block is comprised of compressed particles of sodium chloride.

In some particular embodiments which comprise a salt block (24), the salt block (24) may be a manufactured salt block comprised of particles of sodium chloride which are subjected to relatively high pressure (in the order of several hundred tonnes per salt block) in a mold in order to physically unite the particles of sodium chloride. Suitable manufactured salt blocks comprised of compressed particles of sodium chloride are commonly manufactured by many salt producers for use as salt licks for livestock and other animals and for use in water softening applications.

Particular suitable manufactured salt blocks may include those manufactured by The Canadian Salt Company Limited of Pointe-Claire, Quebec, sold under the WINDSOR trade-mark, and sold as "stock salt". Exemplary manufactured salt block products sold under the WINDSOR trade-mark may include Cobalt Iodized Stock Salt, Iodized Stock Salt and/or Plain White Stock Salt.

The required size and shape of the salt block (24) is dependent upon the manual contact device (20) with which the antimicrobial contact surface (22) is to be associated. The salt block (24) may be sized and shaped from a larger block of salt by cutting, grinding, carving and/or by some other suitable process. Alternatively, in the case of a manufactured salt block, the salt block (24) may be manufactured to provide a desired size and shape by molding and/or by some other suitable process.

Referring to FIGS. 1-8, in some embodiments, the salt block (24) may be sized and shaped to be attached to, connected with, or integrally formed with a manual contact device (20) as an antimicrobial contact surface (22).

In such embodiments, the salt block (24) may be attached to or connected with the manual contact device (20) in any suitable manner.

As one non limiting example, in some particular embodiments, tape (not shown) may be applied to an existing manual contact device (20), an adhesive (not shown) may be applied to the tape (not shown), and the salt block (24) may be attached to or connected with the tape (not shown) by the adhesive (not shown). This system and similar systems for attaching or connecting the salt block (24) to or with the manual contact device (20) facilitate relatively easy "retrofitting" of an existing manual contact device (20) to incorporate a salt block (24) and also facilitate relatively easy removal of the salt block (24) from the manual contact device (20) in order to replace the salt block (24) as may be required.

Figure 1A:
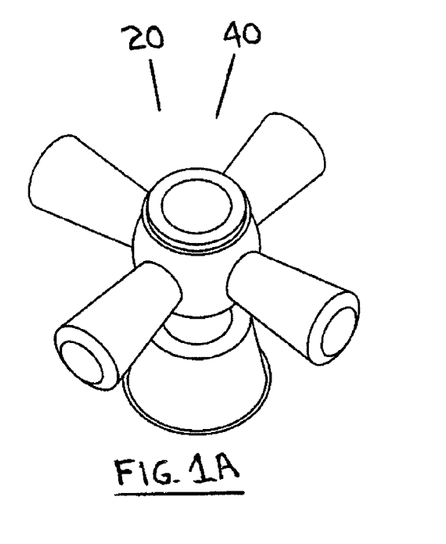
FIG. 1A and FIG. 1B are pictorial views respectively of a manual contact device and a manual contact device comprising a salt block as an antimicrobial contact surface, wherein the manual contact device is a tap handle.
Figure 1B:
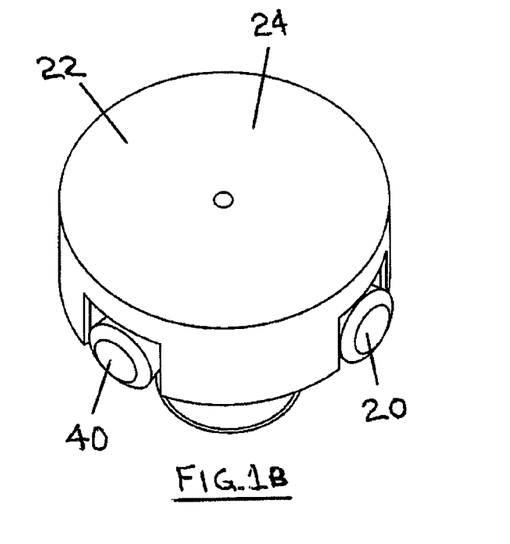

Referring to FIG. 1 (including FIG. 1A and FIG. 1B), the manual contact device (20) is a tap handle (40). In FIG. 1B, the antimicrobial contact surface (22) is a salt block (24) which is attached to or connected with the tap handle (40) in some suitable manner.

Figure 2A:
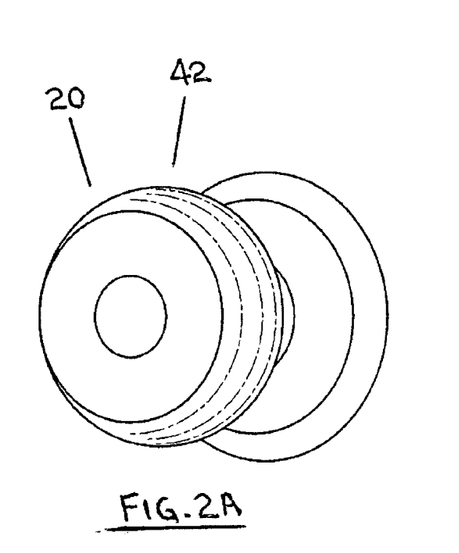
FIG. 2A and FIG. 2B are pictorial views respectively of a manual contact device and a manual contact device comprising a salt block as an antimicrobial contact surface, wherein the manual contact device is a door knob.
Figure 2B:
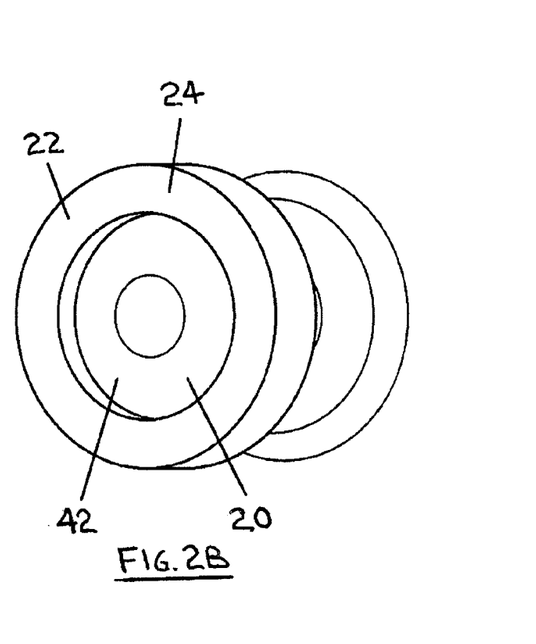

Referring to FIG. 2 (including FIG. 2A and FIG. 2B), the manual contact device (20) is a door knob (42). In FIG. 2B, the antimicrobial contact surface (22) is a salt block (24) which is attached to or connected with the door knob (42) in some suitable manner.

Figure 3A:
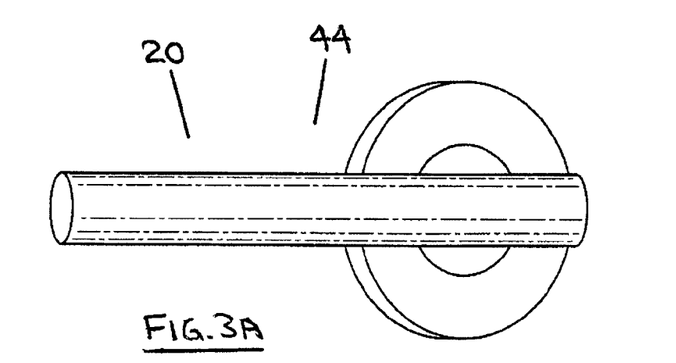
FIG. 3A and FIG. 3B are pictorial views respectively of a manual contact device and a manual contact device comprising a salt block as an antimicrobial contact surface, wherein the manual contact device is a door handle.
Figure 3B:
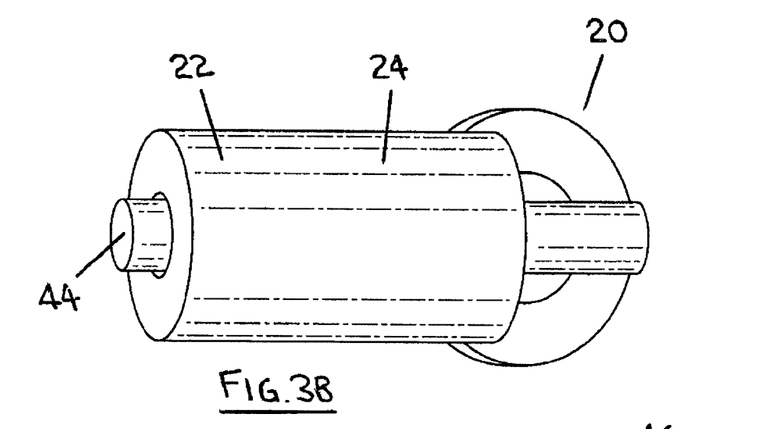

Referring to FIG. 3 (including FIG. 3A and FIG. 3B), the manual contact device (20) is a door handle (44). In FIG. 3B, the antimicrobial contact surface (22) is a salt block (24) which is attached to or connected with the door handle (44) in some suitable manner.

Figure 4A:
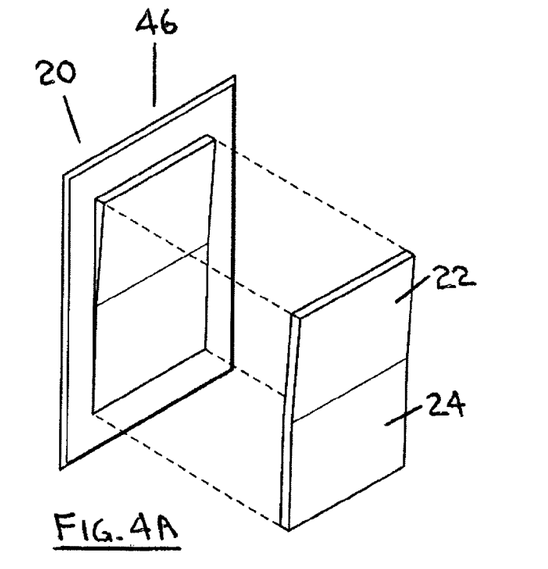
FIG. 4A and FIG. 4B are pictorial views respectively of a manual contact device and a manual contact device comprising a salt block as an antimicrobial contact surface, wherein the manual contact device is a light switch.
Figure 4B:
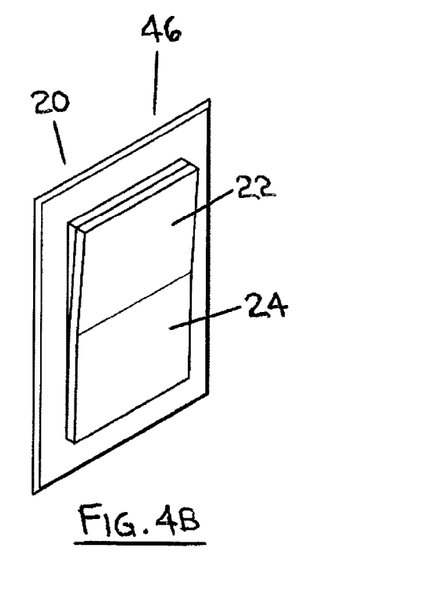

Referring to FIG. 4 (including FIG. 4A and FIG. 4B), the manual contact device (20) is a light switch (46). In FIG. 4B, the antimicrobial contact surface (22) is a salt block (24) which is attached to or connected with the light switch (46) in some suitable manner.

Figure 5A:
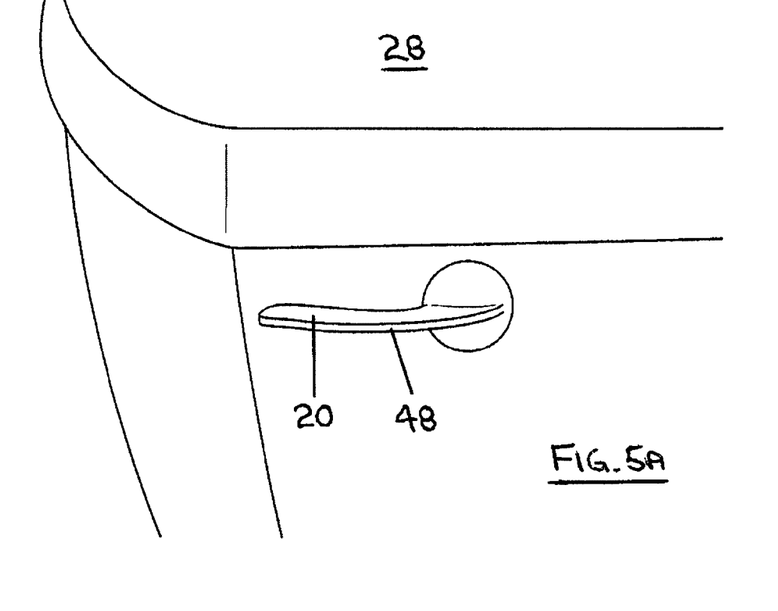
FIG. 5A and FIG. 5B are pictorial views respectively of a manual contact device and a manual contact device comprising a salt block as an antimicrobial contact surface, wherein the manual contact device is a toilet flush actuator.
Figure 5B:
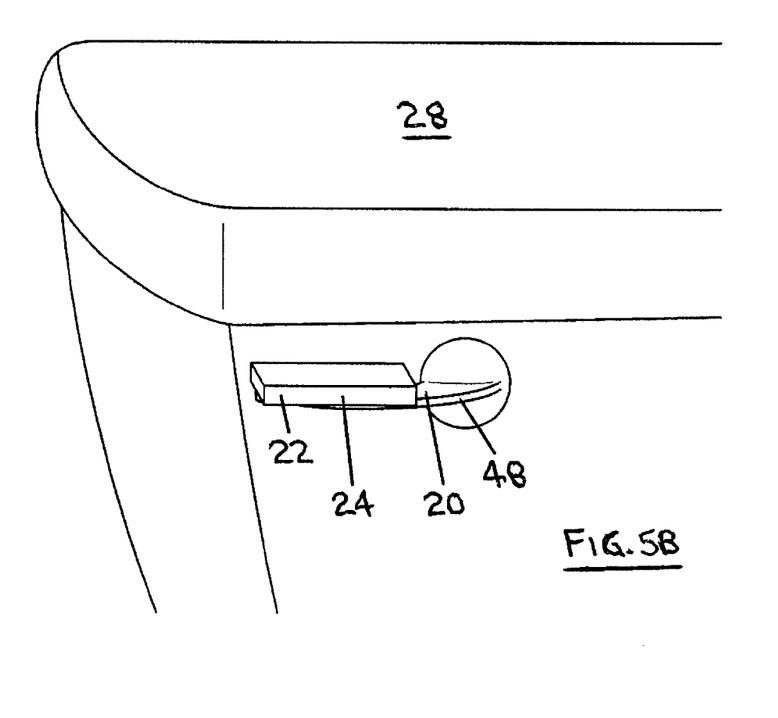

Referring to FIG. 5 (including FIG. 5A and FIG. 5B), the manual contact device (20) is a toilet flush actuator (48). In FIG. 5B, the antimicrobial contact surface (22) is a salt block (24) which is attached to or connected with the toilet flush actuator (48) in some suitable manner.

Figures 6A, 6B:
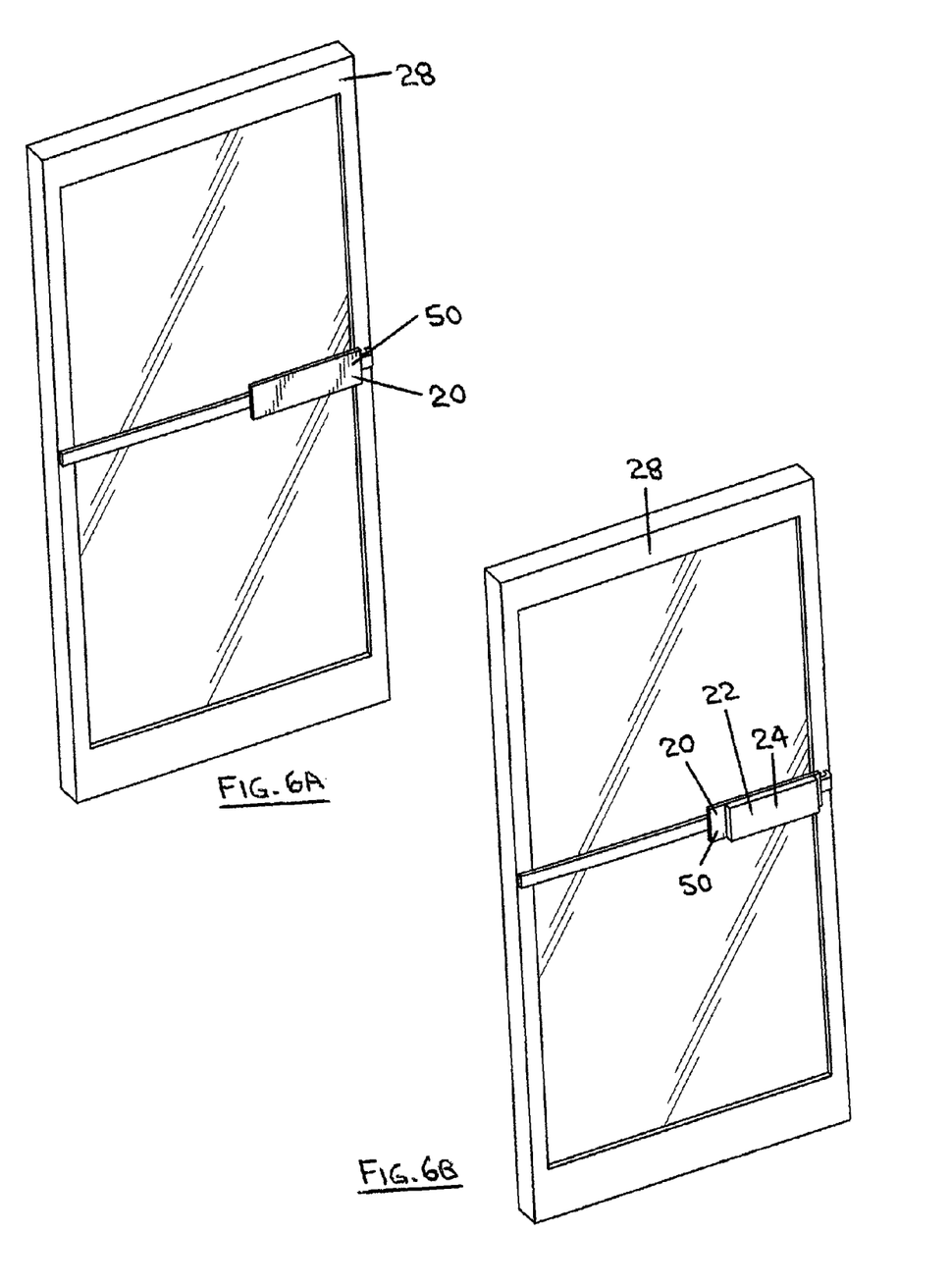
FIG. 6A and FIG. 6B are pictorial views respectively of a manual contact device and a manual contact device comprising a salt block as an antimicrobial contact surface, wherein the manual contact device is a door push bar/railing.

Referring to FIG. 6 (including FIG. 6A and FIG. 6B), the manual contact device (20) is a door push bar or railing (50). In FIG. 6B, the antimicrobial contact surface (22) is a salt block (24) which is attached to or connected with the door push bar or railing (50) in some suitable manner.

Figures 7A, 7B:
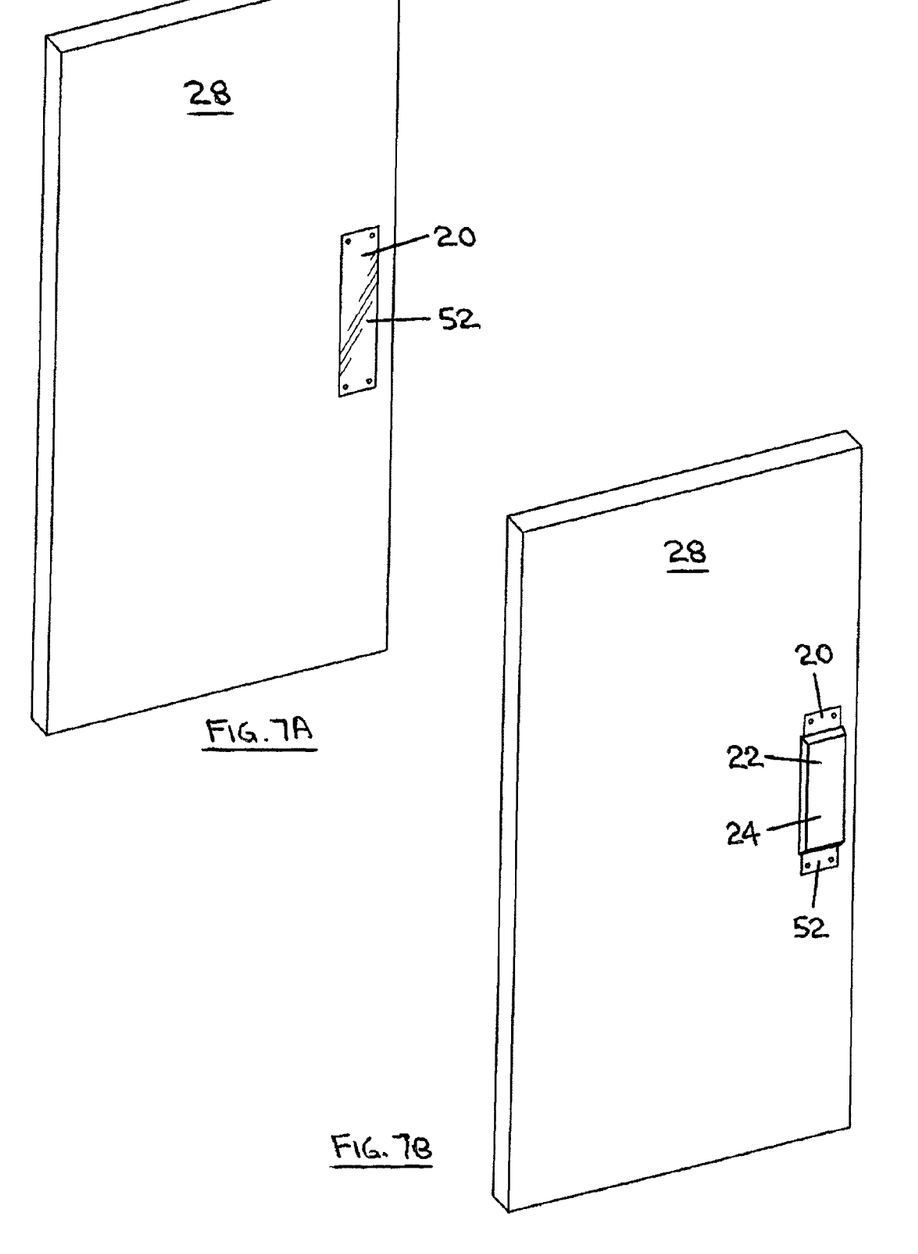
FIG. 7A and FIG. 7B are pictorial views respectively of a manual contact device and a manual contact device comprising a salt block as an antimicrobial contact surface, wherein the manual contact device is a door push plate.

Referring to FIG. 7 (including FIG. 7A and FIG. 7B), the manual contact device (20) is a door push plate (52). In FIG. 7B, the antimicrobial contact surface (22) is a salt block (24) which is attached to or connected with the door push plate (52) in some suitable manner.

Figure 8:
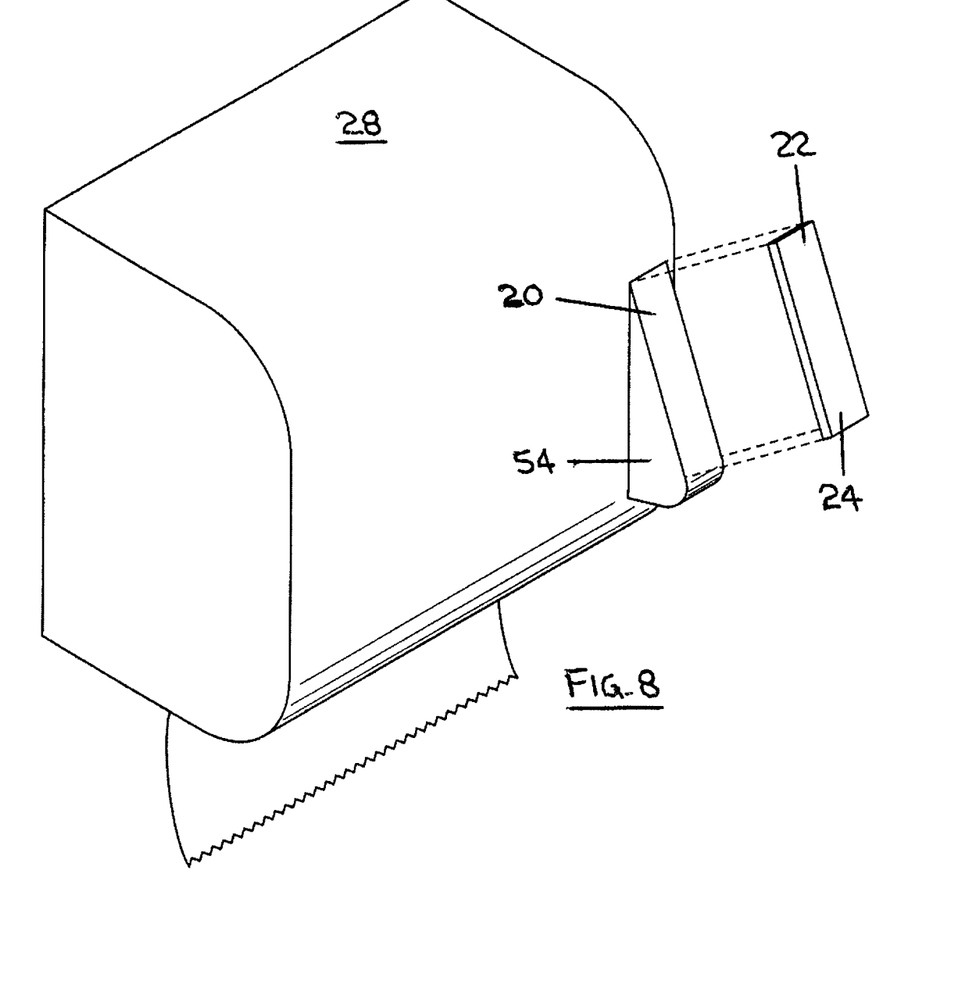
FIG. 8 is a pictorial view respectively of a manual contact device comprising a salt block as an antimicrobial contact surface, wherein the manual contact device is a dispenser actuator.
Figure 9:
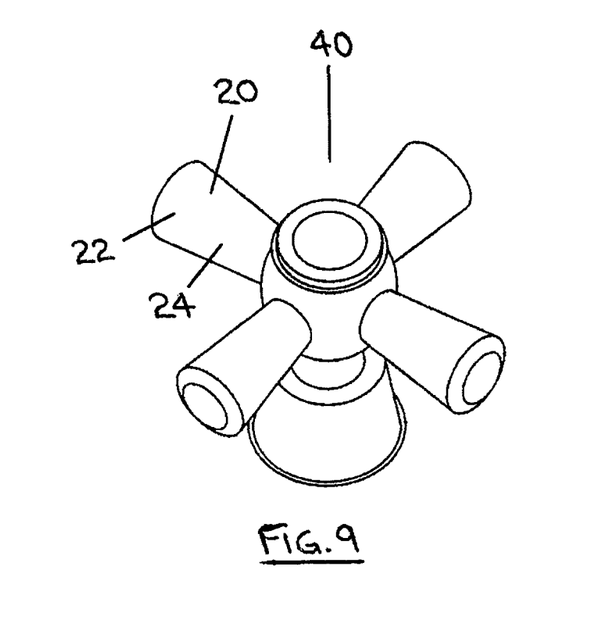
FIG. 9 is a pictorial view of a tap handle as a manual contact device which is formed from and consists essentially of a salt block so that the salt block provides both the manual contact device and the antimicrobial contact surface.
Figure 10:
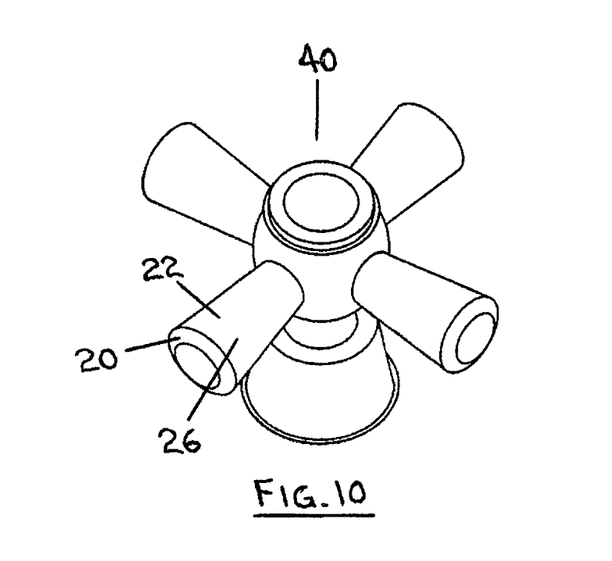
FIG. 10 is a pictorial view of a tap handle as a manual contact device which is provided with a deposit of sodium chloride so that the deposit provides the antimicrobial contact surface.

Referring to FIG. 8, the manual contact device (20) is a dispenser actuator (54). In FIG. 8, the antimicrobial contact surface (22) is a salt block (24) which is attached to or connected with the dispenser actuator (54) in some suitable manner.

In some embodiments, the salt block (24) may be sized and shaped so that the manual contact device (20) is formed from and consists essentially of the salt block (24). In such embodiments, the salt block (24) may essentially serve as the manual contact device (20) and may be sized and shaped similar to a conventional manual contact device (20). In an exemplary embodiment depicted in FIG. 9, a salt block (24) is sized and shaped to form a tap handle (40) as a manual contact device (20).

In some embodiments, sodium chloride may be deposited on the manual contact device (20) to provide the antimicrobial contact surface (22) as a deposit (26) on the manual contact device (20). In an exemplary embodiment depicted in FIG. 10, a deposit (26) comprising sodium chloride is coated on a tap handle (40) as a manual contact device (20) to provide the antimicrobial contact surface (22) on the tap handle (40).

Figure 11:
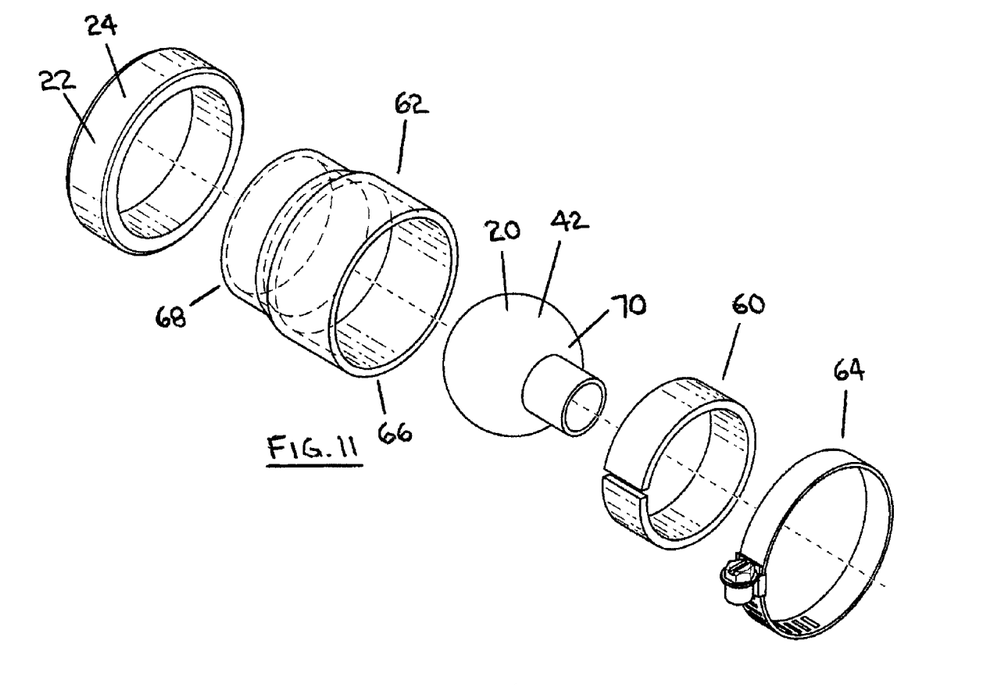
FIG. 11 is an exploded assembly view of a system for attaching or connecting a salt block to a manual contact device, wherein the manual contact device is a door knob.
Figure 12:
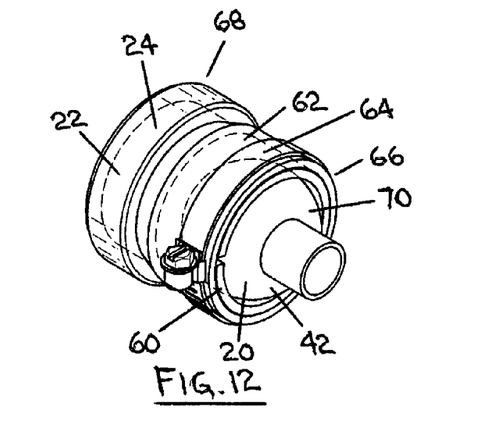
FIG. 12 is a pictorial view of the system depicted in FIG. 9, as assembled on a door knob.

Referring to FIGS. 11-12, a particular system is depicted for attaching or connecting a salt block (24) to a manual contact device (20), wherein the manual contact device (20) is a door knob (42).

Referring to FIG. 11, the system is comprised of a split collet (60), a coupler (62) and a coupler clamp (64). The coupler (62) has a first end (66) and a second end (68). The split collet (60) is sized to encircle the door knob (42) behind the largest dimension of the door knob (42). The first end (66) of the coupler (62) is sized to fit over the split collet (60), and the salt block (24) is sized to fit over the second end (68) of the coupler (62).

The salt block (24) may be attached to or connected with the second end (68) of the coupler (62) with an adhesive, with two-sided tape, or in any other suitable manner. The split collet (60) may be passed over a rear section (70) of the door knob (42) behind the largest dimension of the door knob (42), the first end (66) of the coupler (62) may be passed over the split collet (60), and the coupler clamp (64) may then be tightened in order to secure the first end (66) of the coupler (62) around the split collet (60) and thus fasten the system to the door knob (42). In FIG. 12, the system is shown fastened to a door knob (42).

In the method of the invention, a manual contact device (20) is provided with an antimicrobial contact surface (22), wherein the antimicrobial contact surface (22) is comprised of sodium chloride.

In some embodiments, the antimicrobial contact surface (22) may be a salt block (24) comprised of sodium chloride. In such embodiments, the salt block (24) may be attached to, connected with, or integrally formed with a manual contact device (20), the manual contact device (20) may be formed from the salt block (24) as the antimicrobial contact surface (22), and/or the manual contact device (20) may consist essentially of the salt block (24).

In some embodiments, the antimicrobial contact surface (22) may be a deposit (26) comprising sodium chloride which is deposited on all or a portion of the manual contact device (20) in order to provide the antimicrobial contact surface (22).

Once the manual contact device (20) has been provided with the antimicrobial contact surface (22), subsequent manual contact with the antimicrobial contact surface (22) by a first person (not shown) may result in the transfer of microorganisms to the antimicrobial contact surface (22). These microorganisms will be exposed to the sodium chloride contained in the antimicrobial contact surface (22) and may experience an antimicrobial effect because of the sodium chloride. As a result, subsequent manual contact with the antimicrobial contact surface (22) by a second person (not shown) may result in a reduction in the transfer of microorganisms from the antimicrobial contact surface (22) to the second person than would be the case if the manual contact device (20) were not provided with the antimicrobial contact surface (22).

The above sequence of manual contact with the antimicrobial contact surface (22) may be repeated many times by the first person, the second person, and/or by other persons. Although each occurrence of manual contact will provide an opportunity for the transfer of microorganisms to and from the antimicrobial contact surface (22), the extent of the transfer of microorganisms may be reduced as a result of an antimicrobial effect provided by the antimicrobial contact surface (22).

The antimicrobial contact surface (22) may be replaced as needed if the antimicrobial contact surface (22) becomes depleted, soiled and/or damaged over time.

EXAMPLES

The antimicrobial effect of three different types of salt block (24) was evaluated by laboratory tests. The laboratory tests were performed upon samples of two different types of manufactured salt block and upon samples of a naturally occurring salt block.

The samples were tested against a range of bacterial cultures that are commonly found in the environment. There were two gram positive bacteria tested (*Staphylococcus aureus* ATCC #6538 and *Bacillus subtillis* ATCC #6633) and three gram negative bacteria tested (*Escherichia coli* ATCC #9027, *Salmonella enteric* ATCC #13311, and *Pseudomonas aeruginosa* ATCC #9027).

The samples were prepared by cutting the salt blocks into approximately 6.5 centimeter×6.5 centimeter squares. Controls made of 22 gauge T316L Stainless Steel of the same size were tested alongside the salt block samples.

Overnight cultures of each bacterium were prepared and diluted in stages to two different levels. A first level of diluted culture was used to spike the salt block samples, and was then diluted further to provide a second level of diluted culture which was used to spike the controls.

The diluted cultures were spread onto the samples and controls using a sterile spreader and were allowed to dry for varying periods of time (1 minute, 5 minutes, 15 minutes). A Tryptic Soy Agar+Lecithin and Polysorbate (TSA+LP) contact plate was pressed onto the surface of each sample and control, ensuring that it did not slide. The TSA+LP contact plates were incubated at 32.5±2.5 degrees Celsius until accurate counts could be determined (i.e., for about 24 hours).

The log value of the samples and controls and the log reduction for each sample as compared to the control was calculated from the resulting data. Log reduction is a way to express levels of decreased bacterial load by factors of 10. A 1.0 log reduction is equivalent to a 90 percent reduction in bacterial load. A 2.0 log reduction is equivalent to a 99 percent reduction in bacterial load. A 3.0 log reduction is equivalent to a 99.9 percent reduction in bacterial load.

CFU/ml=(number of CFU)×(Dilution Factor)

Log Reduction=($\log_{10}$ Control CFU/ml)−($\log_{10}$ Sample CFU/ml)

% Reduction in Bacterial Load=100−$10^{(2-Log\ Reduction)}$ (where CFU=colony forming unit)

Example 1

The samples were prepared from a manufactured salt block comprised of compressed particles of sodium chloride. The manufactured salt block was manufactured by The Canadian Salt Company Limited of Pointe-Claire, Quebec, is sold under the trade-mark WINDSOR, and is sold under the product name Cobalt Iodized Stock Salt. The guaranteed analysis of the salt block as indicated on the product label was 99.0% sodium chloride, 70 mg/kg iodine, and 40 mg/kg cobalt.

|  |  | Controls |  | Samples |  |  |  |
| --- | --- | --- | --- | --- | --- | --- | --- |
| Bacteria | Time Period | CFU/ml | Log Value | CFU/ml | Log Value | Log Reduction | % Reduction |
| Staphylococcus aureus | 1 min | $3.3 \times 10^7$ | 7.52 | $2.6 \times 10^6$ | 6.41 | 1.11 | 92.2 |
|  | 5 min | $1.7 \times 10^7$ | 7.23 | $1.1 \times 10^6$ | 6.04 | 1.19 | 93.5 |
|  | 15 min | $2.7 \times 10^7$ | 7.43 | $1.3 \times 10^6$ | 6.11 | 1.32 | 95.2 |
| Pseudomonas aeruginosa | 1 min | $1.3 \times 10^7$ | 7.11 | $>3.0 \times 10^4$ | ≥4.48 | ≤2.63 | ≤99.8 |
|  | 5 min | $7.5 \times 10^6$ | 6.88 | $>3.0 \times 10^4$ | ≥4.48 | ≤2.40 | ≤99.6 |
|  | 15 min | $1.1 \times 10^7$ | 7.04 | $7.0 \times 10^3$ | 3.85 | 3.19 | 99.9 |
| Escherichia coli | 1 min | $2.3 \times 10^7$ | 7.36 | $1.9 \times 10^5$ | 5.28 | 2.08 | 99.2 |
|  | 5 min | $3.3 \times 10^7$ | 7.52 | $1.2 \times 10^5$ | 5.08 | 2.44 | 99.6 |
|  | 15 min | $2.3 \times 10^7$ | 7.36 | $9.1 \times 10^4$ | 4.96 | 2.40 | 99.6 |
| Bacillus subtillis | 1 min | $1.3 \times 10^5$ | 5.11 | $9.2 \times 10^2$ | 2.96 | 2.15 | 99.3 |
|  | 5 min | $1.1 \times 10^5$ | 5.04 | $2.4 \times 10^2$ | 2.38 | 2.66 | 99.8 |
|  | 15 min | $7.0 \times 10^4$ | 4.85 | $2.7 \times 10^2$ | 2.43 | 2.42 | 99.6 |

Example 2

The samples were prepared from a manufactured salt block comprised of compressed particles of sodium chloride. The manufactured salt block was manufactured by The Canadian Salt Company Limited of Pointe-Claire, Quebec, is sold under the trade-mark WINDSOR, and is sold under the product name Iodized Stock Salt. The guaranteed analysis of the salt block as indicated on the product label was 99.0% sodium chloride and 70 mg/kg iodine.

|  |  | Controls |  | Samples |  |  |  |
| --- | --- | --- | --- | --- | --- | --- | --- |
| Bacteria | Time Period | CFU/ml | Log Value | CFU/ml | Log Value | Log Reduction | % Reduction |
| Staphylococcus aureus | 1 min | $6.5 \times 10^7$ | 7.81 | $2.0 \times 10^6$ | 6.30 | 1.51 | 96.9 |
|  | 5 min | $5.3 \times 10^7$ | 7.72 | $3.5 \times 10^5$ | 5.54 | 2.18 | 99.3 |
| Pseudomonas aeruginosa | 1 min | $4.7 \times 10^7$ | 7.67 | $>3.0 \times 10^5$ | ≥5.48 | ≤2.19 | ≤99.4 |
|  | 5 min | $1.24 \times 10^7$ | 7.09 | $3.9 \times 10^4$ | 4.59 | 2.50 | 99.7 |
| Escherichia coli | 1 min | $2.8 \times 10^7$ | 7.45 | $1.5 \times 10^6$ | 6.16 | 1.29 | 94.9 |
|  | 5 min | $3.0 \times 10^7$ | 7.48 | $4.7 \times 10^4$ | 4.67 | 2.81 | 99.8 |
| Salmonella enterica | 1 min | $2.6 \times 10^7$ | 7.41 | $7.1 \times 10^5$ | 5.85 | 1.56 | 97.2 |
|  | 5 min | $2.7 \times 10^7$ | 7.43 | $3.0 \times 10^5$ | 5.48 | 1.95 | 98.9 |

Example 3

The samples were prepared from a naturally occurring salt block. The naturally occurring salt block was mined in Pakistan by Pakistan Minerals Development Corporation and sold by Gamma Salt Cristals Ltd. of Toronto, Ontario under the trade-mark GAMMA and product name GAMMA Genuine Himalayan Crystal Salt. The chemical composition of the GAMMA Genuine Himalayan Crystal Salt according to a certificate issued by DM Brothers Importers and Exporters of Lahore, Pakistan is 98.86% sodium chloride, 0.25% sodium sulphate, 0.63% calcium magnesium, 0.04% water and 0.1% insoluble material.

|  |  | Controls |  | Samples |  |  |  |
| --- | --- | --- | --- | --- | --- | --- | --- |
| Bacteria | Time Period | CFU/ml | Log Value | CFU/ml | Log Value | Log Reduction | % Reduction |
| Staphylococcus aureus | 1 min | $6.5 \times 10^7$ | 7.81 | $>3.0 \times 10^6$ | ≥6.48 | ≤1.33 | ≤95.3 |
|  | 5 min | $5.3 \times 10^7$ | 7.72 | $>3.0 \times 10^6$ | ≥6.48 | ≤1.24 | ≤94.2 |
| Pseudomonas aeruginosa | 1 min | $4.7 \times 10^7$ | 7.67 | $>3.0 \times 10^6$ | ≥6.48 | ≤1.19 | ≤93.5 |
|  | 5 min | $1.24 \times 10^7$ | 7.09 | $>3.0 \times 10^6$ | ≥6.48 | ≤0.61 | ≤75.5 |
| Escherichia coli | 1 min | $2.8 \times 10^7$ | 7.45 | $>3.0 \times 10^6$ | ≥6.48 | ≤0.97 | ≤89.3 |
|  | 5 min | $3.0 \times 10^7$ | 7.48 | $8.7 \times 10^5$ | 5.94 | 1.54 | 97.1 |
| Salmonella enterica | 1 min | $2.6 \times 10^7$ | 7.41 | $>3.0 \times 10^6$ | ≥6.48 | ≤0.93 | ≤88.0 |
|  | 5 min | $2.7 \times 10^7$ | 7.43 | $3.3 \times 10^6$ | 6.51 | 0.92 | 87.9 |

Observations from Examples

With respect to the bacteria tested, the samples of Example 1 and Example 2 appeared to provide a superior antimicrobial effect than the samples of Example 3. Without intending to be bound by theory, a number of possible explanations may be formulated for the apparent superior antimicrobial performance of a manufactured salt block in comparison with a natural salt block. One possible explanation may be the homogeneity in composition and structure which can be achieved in a manufactured salt block. A second possible explanation may be the relatively small particle size of the particles of sodium chloride which are used to produce the manufactured salt block.

In this document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The invention claimed is:

1. A manual contact device comprising an antimicrobial contact snake. wherein the antimicrobial contact surface is a salt block, and wherein the manual contact device is selected from the group of manual contact devices consisting of a door knob, a door handle, a door push plate, a door push bar a light switch, a railing, a tap handle, a toilet flush actuator and a dispenser actuator, wherein the salt block is attached to the manual contact device.

2. The manual contact device as claimed in claim 1 wherein the salt block is a naturally occurring salt block.

3. The manual contact device as claimed in claim 1 wherein the salt block is a manufactured salt block comprised of compressed particles of sodium chloride.

4. The manual contact device as claimed in claim 1 wherein the salt block consists essentially of sodium chloride.

5. A manual contact device comprising an antimicrobial contact surface, wherein the antimicrobial contact surface is a salt block, and wherein the manual contact device is selected from the group of manual contact devices consisting of a door knob, a door handle, a door push plate, a door push bar, a light switch, a railing, a tap handle, a toilet flush actuator, and a dispenser actuator, wherein the antimicrobial contact surface is a deposit which is deposited on the manual contact device.

6. The manual contact device as claimed in claim 5 wherein the salt block is a naturally occurring salt block.

7. The manual contact device as claimed in claim 5 wherein the salt block is a manufactured salt block comprised of compressed particles of sodium chloride.

8. The manual contact device as claimed in claim 5 wherein the salt block consists essentially of sodium chloride.

9. method for reducing a transfer of microorganisms by manual contact with a manual contact device, the method comprising providing the manual contact device with an antimicrobial contact surface wherein the antimicrobial contact surface is a salt block, and wherein the manual contact device is selected from the group of manual contact devices consisting of a door knob, a door handle, a door push plate, a door push bar, a light switch, a railing a tap handle, a toilet flush actuator, and a dispenser actuator, wherein providing the manual contact device with the antimicrobial contact surface is comprised of attaching the salt block to the manual contact device.

10. The method as claimed in claim 9, further comprising manually contacting the antimicrobial contact surface.

11. The method as claimed in claim 9 wherein the salt block is a naturally occurring salt block.

12. The method as claimed in claim 9 wherein the salt block is a manufactured salt block comprised of compressed particles of sodium chloride.

13. The method as claimed in claim 9 wherein the salt block consists essentially of sodium chloride.

14. A method for reducing a transfer of microorganisms by manual contact with a manual contact device, the method comprising providing the manual contact device with an antimicrobial contact surface, wherein the antimicrobial contact surface is a salt block, and wherein the manual contact device is selected from the group of manual contact devices consisting of a door knob, a door handle, a door push plate, a door push bar, a light switch, railing, a tap handle, a toilet flush actuator, and a dispenser actuator, wherein the antimicrobial contact surface is a deposit which is deposited on the manual contact device.

15. The method as claimed in claim 14, further comprising manila iv contacting the antimicrobial contact surface.

16. The method as claimed in claim 14 wherein the salt block is a naturally occurring salt block.

17. The method as claimed in claim 14 wherein the salt block is a manufactured salt block comprised of compressed particles of sodium chloride.

18. The method as claimed in claim 14 wherein the salt block consists essentially of sodium chloride.

* * * * *